United States Patent
Kawata et al.

(10) Patent No.: US 9,040,927 B2
(45) Date of Patent: May 26, 2015

(54) RADIATION DETECTION APPARATUS

(71) Applicants: Go Kawata, Kawasaki (JP); Hideyuki Funaki, Tokyo (JP); Honam Kwon, Kawasaki (JP); Risako Ueno, Tokyo (JP); Kazuhiro Suzuki, Tokyo (JP)

(72) Inventors: Go Kawata, Kawasaki (JP); Hideyuki Funaki, Tokyo (JP); Honam Kwon, Kawasaki (JP); Risako Ueno, Tokyo (JP); Kazuhiro Suzuki, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 79 days.

(21) Appl. No.: 13/713,523

(22) Filed: Dec. 13, 2012

(65) Prior Publication Data

US 2013/0248724 A1 Sep. 26, 2013

(30) Foreign Application Priority Data

Mar. 21, 2012 (JP) ................. 2012-064247

(51) Int. Cl.
  *G01T 1/20* (2006.01)
(52) U.S. Cl.
  CPC ............. *G01T 1/2002* (2013.01); *G01T 1/2018* (2013.01)
(58) Field of Classification Search
  CPC ........ G01T 1/20; G01T 1/2002; G01T 1/2018
  USPC .................... 250/366, 368, 370.11
  See application file for complete search history.

(56) References Cited

U.S. PATENT DOCUMENTS

| 5,617,463 A * | 4/1997 | Beierlein ................. 378/98.3 |
| 2012/0228497 A1 | 9/2012 | Suzuki et al. |

FOREIGN PATENT DOCUMENTS

| JP | 2004-150932 | | 5/2004 |
| JP | 2006-242949 | A | 9/2006 |
| JP | 2008-311651 | | 12/2008 |
| JP | 2009-222578 | A | 10/2009 |
| JP | 2009222578 | A * | 10/2009 |
| JP | 2010-522806 | | 7/2010 |
| WO | WO 2008/004547 | A1 | 1/2008 |

OTHER PUBLICATIONS

Japanese Office Action issued on Jun. 27, 2014 in corresponding Japanese Application No. 2012-064247 with English translation, citing documents AO, AP, and AQ therein (6 pages).
Office Action issued Jan. 30, 2015 in Japanese Patent Application No. 2012-064247 (with English translation).

* cited by examiner

*Primary Examiner* — Mark R Gaworecki
(74) *Attorney, Agent, or Firm* — Oblon, McClelland, Maier & Neustadt, L.L.P.

(57) ABSTRACT

A radiation detection apparatus according to an embodiment includes: a scintillator including a fluorescent material to convert radiation to visible radiation photon; a photon detection device array having a plurality of cells each of which includes a photon detection device to detect visible radiation photon emitted from a fluorescent material in the scintillator and convert the visible radiation photon to an electric signal; and a plurality of lenses provided on cells respectively in association with the cells to cause the visible radiation photon to be incident on the photon detection device in an associated cell.

12 Claims, 18 Drawing Sheets

RADIATION DETECTION APPARATUS

CROSS-REFERENCE TO RELATED APPLICATION

This application is based upon and claims the benefit of priority from prior Japanese Patent Application No. 2012-64247 filed on Mar. 21, 2012 in Japan, the entire contents of which are incorporated herein by reference.

FIELD

Embodiments described herein relate generally to a radiation detection apparatus.

BACKGROUND

In the radiation imaging system such as an X-ray imaging apparatus and a CT (Computerized Tomography) system, generally an X-ray source emits X-rays toward an inspection object or a subject such as a patient or goods. An X-ray beam is attenuated by the inspection object, and then is incident on radiation detectors arranged in an array form. A radiation intensity received in a position of each detector typically depends upon attenuation of X-rays. Each of the detection elements in detectors arranged in an array form generates an electric signal which represents an attenuated beam received by each detection element. These signals are transmitted to a data processing system for an analysis, and an image is finally created by the data processing system.

As for radiation detection, a scheme in which radiation is incident on a fluorescent material such as a scintillator and generated fluorescent light is detected by a photodiode, a photomultiplier tube, or the like is common. There is a property that the number of fluorescent photons emitted from a fluorescent material used at this time is proportionate to radiation energy incident upon the fluorescent material. Therefore, it becomes possible to measure energy of radiation which has been transmitted through an inspection object by counting the number of fluorescent photons emitted from the fluorescent material. It becomes possible to obtain a CT image based upon energy discrimination, i.e., a color CT image by applying this property to CT or the like.

For implementing a CT of photon detection type, detection of the number of fluorescent photons conducted by arranging avalanche photodiodes operating in a Geiger mode as detection elements and counting the number of photons incident on a detector is being studied. As for the avalanche photodiodes operating in the Geiger mode, utilization of a Si material and the like is being studied.

Each of the avalanche photodiodes (hereafter referred to as APDs as well) operating in the Geiger mode is a photodiode which emits one current pulse every photon incident on the photodiode. A current pulse having a wave height proportionate to the number of APDs on which photons are incident is emitted by arranging APDs in an array form. It becomes possible to measure the number of photons incident on the photon detector, i.e., energy of radiation incident on the fluorescent material by pulse height analysis.

As described later, it is found according to a study result of the present inventors that it is impossible to sufficiently take out photons in conversion from radiation to visible light and count visible light without omission, in a conventional radiation detection apparatus which counts X-ray photons by using a light sensing system obtained by combining a scintillator with an APD array.

In the conventional radiation detection apparatus, therefore, the detection efficiency of fluorescent photons emitted from a fluorescent material cannot be enhanced.

DETAILED DESCRIPTION

A radiation detection apparatus according to an embodiment includes: a scintillator including a fluorescent material to convert radiation to visible radiation photon; a photon detection device array having a plurality of cells each of which includes a photon detection device to detect visible radiation photon emitted from a fluorescent material in the scintillator and convert the visible radiation photon to an electric signal; and a plurality of lenses provided on cells respectively in association with the cells to cause the visible radiation photon to be incident on the photon detection device in an associated cell.

First, before describing the embodiments, the course of events for achieving the embodiments will be described below.

Figure 1:
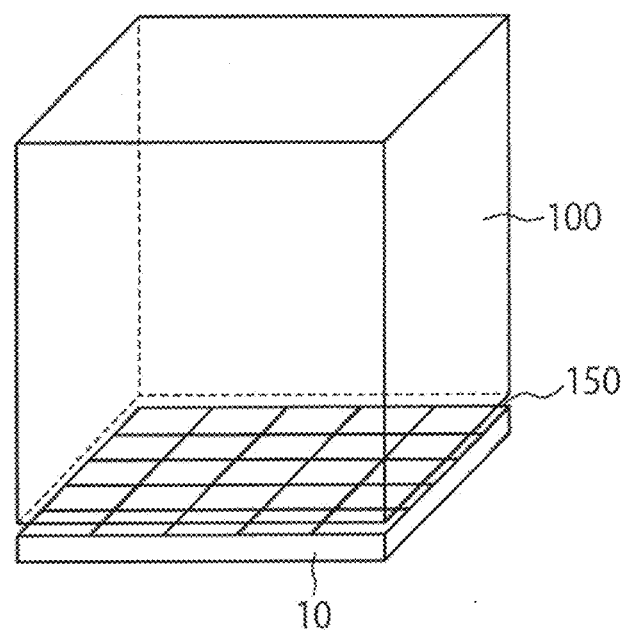
FIG. 1 is a schematic diagram showing an outline of a radiation detection apparatus.

It is now supposed as shown in FIG. 1 that a radiation detection apparatus includes an APD array 10 in which APD cells formed of avalanche photodiodes (APD) of pn-junction type operating in the Geiger mode (GM) are arranged in an array form, and a scintillator 100 including a fluorescent material which generates fluorescent light corresponding to incident X-rays, and the APD array 10 and the scintillator 100 are bonded together with an adhesive layer 150. When APDs operate in the Geiger mode (GM-APD), the electrical signal gain is amount $10^5$/photon.

Figure 2:
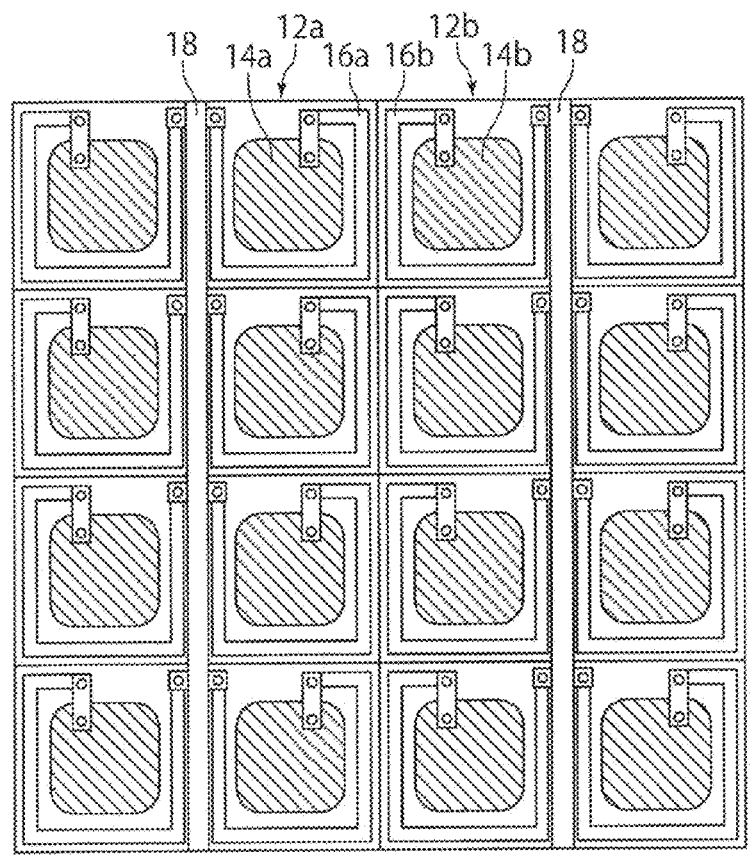
FIG. 2 is a plane view showing an APD array in a radiation detection apparatus.
Figure 3:
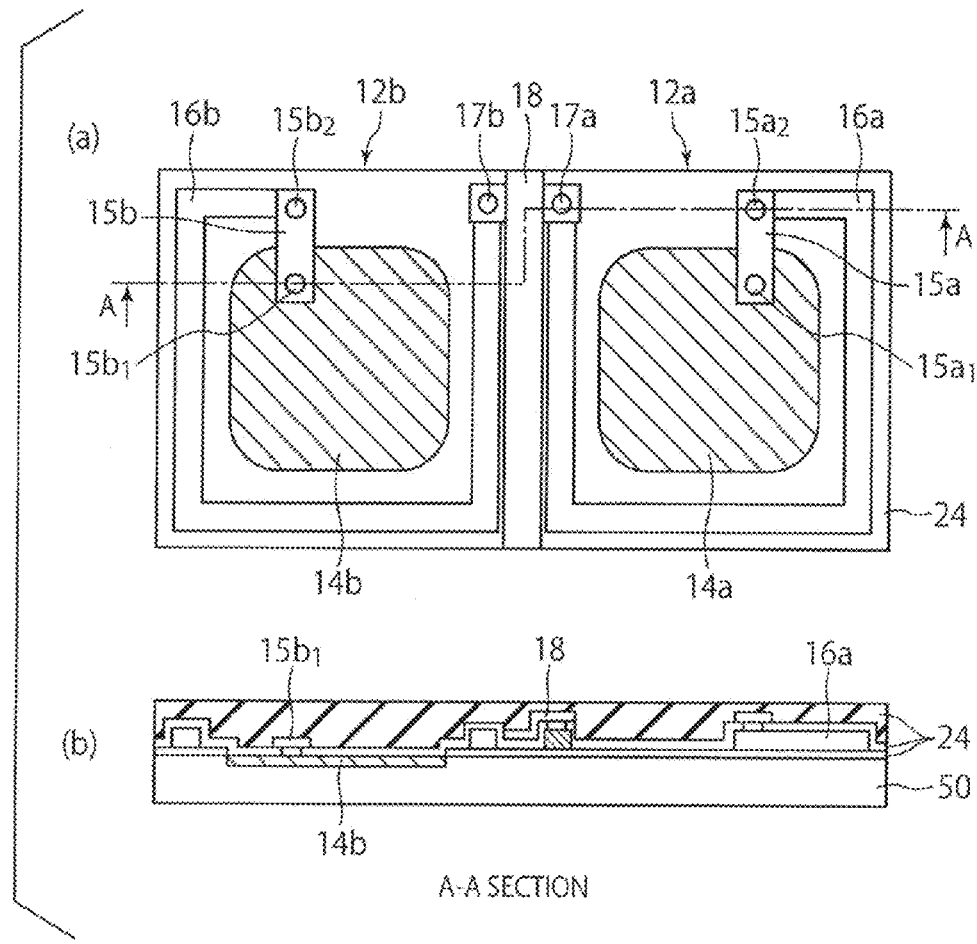
FIGS. 3(a) and 3(b) are a plane view and a sectional view showing APD cells, respectively.

An example of the GM-APD array 10 used in this radiation detection apparatus is shown in FIG. 2. The APD array 10 has a configuration in which two GM-APD cells 12a and 12b form one set and a plurality of sets are arranged in an array form. The GM-APD cell 12a includes a GM-APD having an APD active region 14a and a quench resistor 16a for limiting a current which is output from the APD. Furthermore, the GM-APD cell 12b includes an APD having an APD active region 14b and a quench resistor 16b for limiting a current which is output from the APD. By the way, the quench resistors 16a and 16b are formed of, for example, polysilicon. The APD cells 12a and 12b in respective sets are arranged adjacent to each other in a row direction. An interconnection 18 extending in a column direction is provided between sets which are adjacent to each other in the row direction. In other words, the interconnections 18 are provided on both sides of respective sets in the row direction, and the interconnections 18 become interconnections common to sets arranged in the same column direction. For example, in FIG. 2, with respect to one set, the APD cell 12a is disposed on the left side in the row direction and the APD cell 12b is disposed on the right side. The quench resistor 16a included in a set is provided to connect the active region 14a to the interconnection 18 provided on the left side of the set, and surround the active region 14a on three sides. The quench resistor 16b included in the set is provided to connect the active region 14b to the interconnection 18 provided on the right side of the set, and surround the active region 14b on three sides. In the APD cells 12a and 12b which form a set and which are adjacent to each other, therefore, the quench resistor 16a and the quench resistor 16b are formed to be line-symmetry about a line in the column direction. A plane view of the APD cells 12a and 12b which are adjacent to each other with the interconnection 18 between in the row direction is shown in FIG. 3(a), and a section obtained by cutting with a cut line A-A shown in FIG. 3(a) is shown in FIG. 3(b). The APD active regions 14a and 14b are formed on a semiconductor substrate 50. The active region 14a is connected to a pull-out interconnection 15a via a contact $15a_1$, and the pull-out interconnection 15a is connected to the quench resistor 16a via a contact $15a_2$. The quench resistor 16a is connected to the interconnection 18 via a contact 17a. In the same way, the active region 14b is connected to a pull-out interconnection 15b via a contact $15b_1$, and the pull-out interconnection 15b is connected to the quench resistor 16b via a contact $15b_2$. The quench resistor 16b is connected to the interconnection 18 via a contact 17b. The active regions 14a and 14b, the pull-out interconnections 15a and 15b, the contacts $15a_1$, $15a_2$, $15b_1$, and $15b_2$, the quench resistors 16a and 16b, the contacts 17a and 17b, and the interconnection 18 are covered by interlayer insulation films 24. If the size of the APD cell (length of one side of the cell) becomes large in such an APD array, then the aperture ratio (ratio of the area of the active region to the area of the cell) becomes large and the ratio of a dead space (i.e., a region occupied by the quench resistors 16a and 16b and the like other than the active regions) to the area of the cell becomes small.

For detecting photons enough to discriminate energy of radiation and achieve a sufficient spatial resolution in the radiation detection apparatus, it is necessary to dispose approximately 1,000 APD cells in one spatial resolution area in an array form. For example, for achieving 500 μm which is the resolution of an existing computerized tomography (CT) system, an APD array having approximately 1,000 APD cells arranged in a space of 500 μm square in an array form becomes necessary. In this case, the spacing between APD cells is in the range of approximately 10 μm to 20 μm.

On the other hand, for the APD array to operate in the Geiger mode, the APD array needs to have a sufficient breakdown voltage. Therefore, the APD needs to have an interconnection space which is large enough to obtain the breakdown voltage. Furthermore, when the spacing between APDs is set to be in the range of approximately 10 to 20 μm, optical crosstalk poses a problem. The optical crosstalk is caused by a phenomenon that an incident photon causes avalanche within an APD and a photon generated in the process (e.g hot carrier effect) moves into an adjacent APD.

It is known that the optical crosstalk can be suppressed by providing optical isolation called trench between photodiodes. However, an interconnection space between photodiodes depends upon the breakdown voltage of the photodiodes. Therefore, it is impossible to save the space easily. As a result, the optical crosstalk becomes a cause of lowering the aperture ratio of photodiodes, i.e., the detection efficiency.

If approximately 1,000 photodiodes are provided in 500 $μm^2$ in order to obtain sufficient counting precision when fluorescent light generated in a fluorescent material is incident on a photodiode array operating in the Geiger mode and the number of fluorescent photons is counted, then the interconnection space between photodiodes amounts to at least 70% of the area formed by the photodiode spacing. Therefore, the detection efficiency is lowered by an amount corresponding to the interconnection space.

The present inventors have thought that it is important in increasing the detection efficiency to effectively improve the aperture ratio of the APD cells by making the interconnection space small or providing a novel structure.

Furthermore, the scintillator which is a fluorescent material generates photons depending upon the incident amount of radiation. However, the generated photons are taken out to the outside of the scintillator only in a solid angle depending upon mismatching in refractive index between a bonding agent which is a member for bonding the scintillator to a light sensing element, and the scintillator.

The light taken-out efficiency depends upon selection of these materials. If, for example, LYSO ($Lu_{2(1-x)}Y_{2x}(SiO_4)O$) (refractive index 1.82) is used for the scintillator and an epoxy material (refractive index 1.56) is used for the bonding agent, the light taken-out efficiency is as small as 30%. In this case, specifically when radiation of 120 kV is incident on LYSO, approximately 3,000 photons are generated. Among the photons, however, only less than 1,000 photons can be taken out. In addition, when counting the number of photons by light sensing elements in the latter stage, photons which can be detected truly become less than 300 photons because of the aperture ratio (<30%) of the light sensing elements. In other words, in the medical CT, the detection system formed by combining the scintillator with the APD array cannot count the number of photons enough to have an energy resolution.

When counting photons by a light sensing system formed by combining the scintillator with the APD array, therefore, it is necessary to take out photons sufficiently in conversion of radiation to visible light and count visible light without omission. The present inventors have been able to obtain a radiation detection apparatus as a result of eager study. Hereafter, this radiation detection apparatus will be described as embodiments.

First Embodiment

Figure 4:
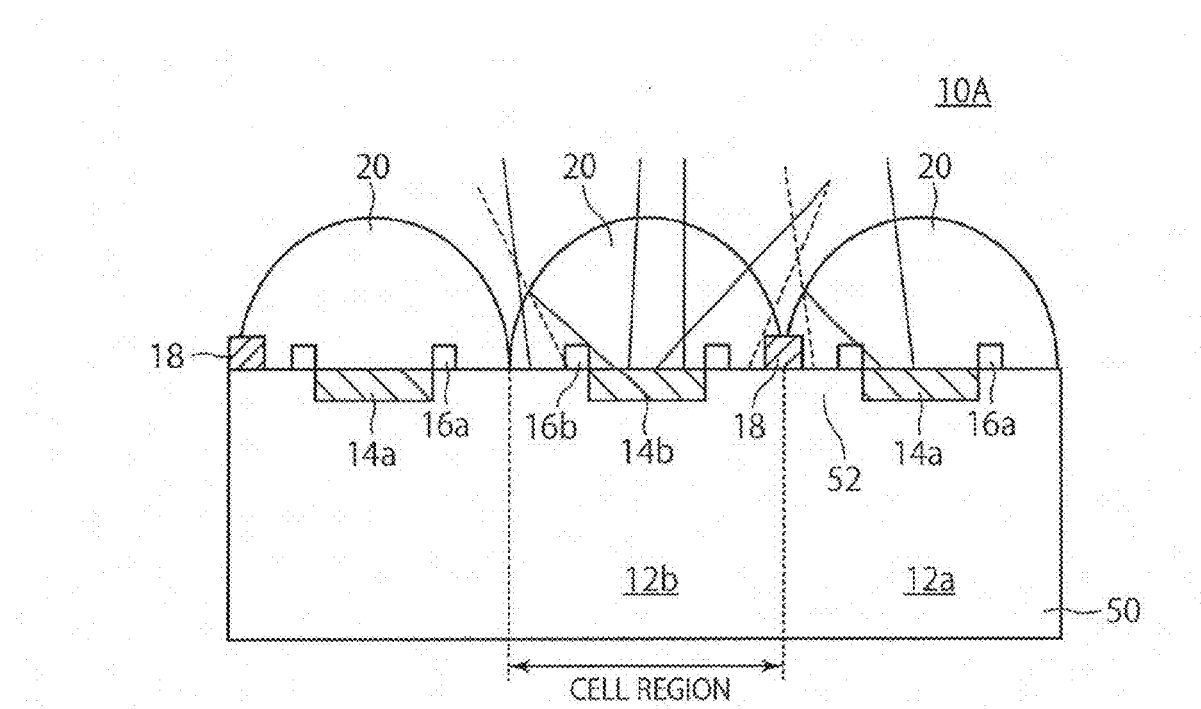
FIG. 4 is a sectional view showing an APD array in a radiation detection apparatus according to a first embodiment.
Figure 5:
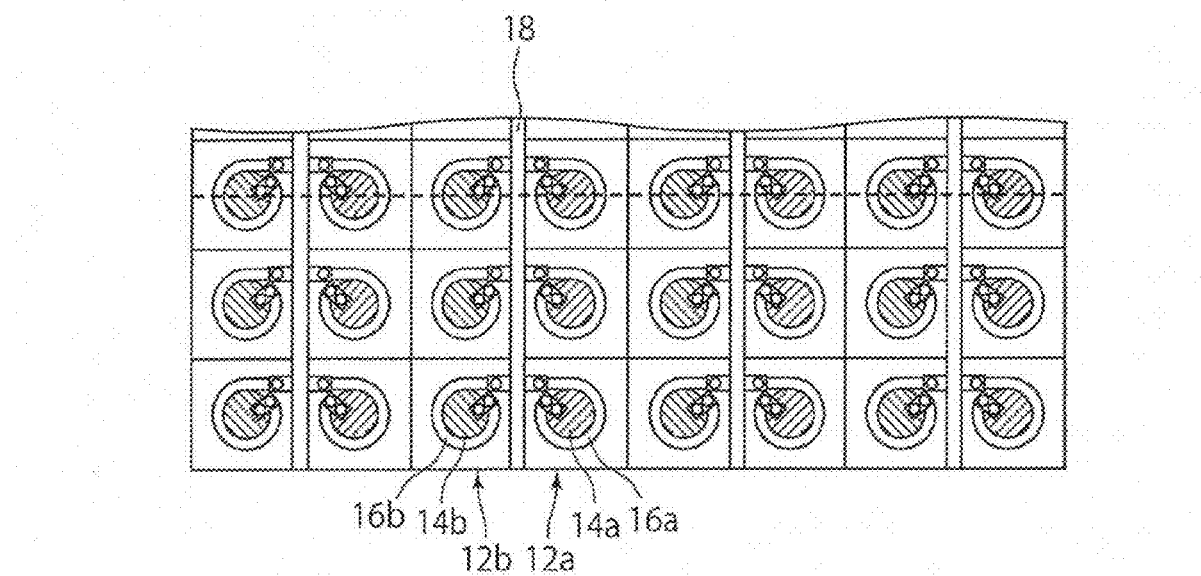
FIG. 5 is a plane view showing an APD array in a radiation detection apparatus according to the first embodiment.
Figure 6:
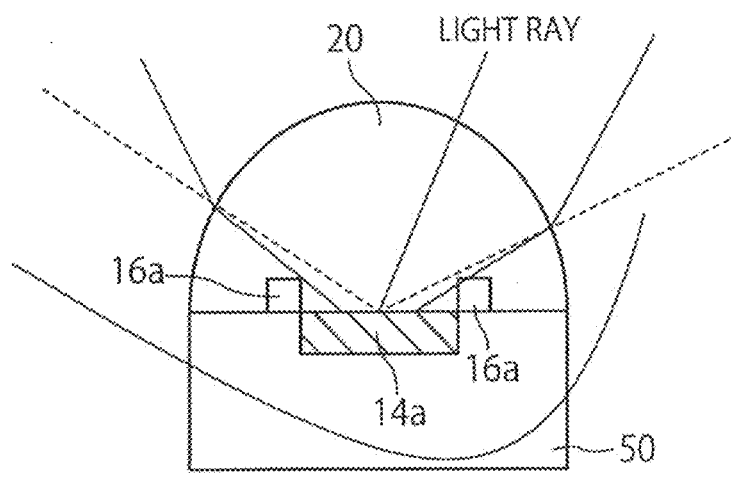
FIG. 6 is a sectional view showing an APD cell in a radiation detection apparatus according to the first embodiment.

A radiation detection apparatus according to a first embodiment will now be described with reference to FIGS. 4 to 6. The radiation detection apparatus in this embodiment has a configuration obtained from that of the radiation detection apparatus shown in FIG. 1 by replacing the APD array 10 with an APD array 10A shown in FIG. 4. In other words, the radiation detection apparatus according to the present embodiment includes a scintillator 100 having a fluorescent material to generate fluorescent photons corresponding to incident energy of X-ray photons, and an APD array 10A formed by arranging APD cells having avalanche photodiodes (APD) which operate in the Geiger mode to detect fluorescent photon generated from the scintillator 100 in an array form. FIG. 4 is a sectional view of the APD array 10A in the radiation detection apparatus according to the present embodiment. The APD array 10A has a configuration obtained from that of the APD array 10 shown in FIGS. 2 to 3(b) by changing the active regions and quench resistors in the APD cells to shapes shown in FIG. 5 and providing a microlens 20 on each APD cell 12. In other words, the active regions 14a and 14b in the APD cells take the shape of a circle and the quench resistors 16a and 16b are formed to surround the active regions 14a and 14b, respectively, as shown in FIG. 5. Furthermore, the microlens 20 takes the shape of, for example, a hemisphere. The microlenses 20 are disposed with their centers aligned substantially with centers of the active regions 14.

As shown in FIG. 5, the GM-APD array 10A has a configuration in which two APD cells 12a and 12b form one set and a plurality of sets are arranged in an array form. The APD cell 12a includes an APD having an APD active region 14a and a quench resistor 16a for limiting a current which is output from the APD. Furthermore, the APD cell 12b includes an APD having an APD active region 14b and a quench resistor 16b for limiting a current which is output from the APD. By the way, the quench resistors 16a and 16b are formed of, for example, polysilicon, and formed on the semiconductor substrate 50 in the APD cells 12a and 12b, respectively, in the same way as the case shown in FIGS. 2 to 3(b).

In the present embodiment, the microlens 20 is provided right above the APD cell in this way. As a result, the effective aperture ratio of the GM-APD array 10A is improved. For example, as shown as to the APD cell 12a in FIG. 6, a light ray perpendicular to the surface of the microlens 20 (a light ray indicated by a dashed line) goes straight on through the microlens 20 without being refracted and is incident on the active region 14a. A light ray (a light ray indicated by a solid line) which inclines from a normal line of the surface of the microlens 20 is refracted by the microlens 20 and incident on the active region 14a. As a result, the effective aperture ratio of the APD array 10A is improved.

In general, in the image sensor, it is conducted to provide a microlens array on the image sensor in order to collect light to a sensor pixel efficiently. In this case, positional relationships between the microlenses and the sensor becomes "main lens-vacuum-microlens array-vacuum-image sensor."

If this relation is applied to the radiation detection apparatus in the present embodiment, the positional relationship becomes "scintillator-vacuum-microlens array-vacuum-APD array." At this time, mismatching of the refractive index is caused between the microlens array and the vacuum and light loss is caused as described above. Since it is desirable to conduct light collecting to the APD array without light loss, the APD array and the microlens array are configured to be bonded together in the present embodiment. FIG. 4 shows this relation conceptually. Differences from the ordinary relation between the image sensor and the lens array are:

1) A convex face of the lens is opposed to a light ray incidence side;

2) It is considered that the opportunity for the light ray incident on a dead space region to be incident on an APD cell is increased by increasing the number of times of refraction;

3) The lens and the APD cell do not form an image forming system. Since multiplication due to the avalanche effect is caused at the time when a photon has reached an arbitrary position of an APD cell active area region, disposition and design of the lens should be conducted to make diffraction brought about by the lens great;

4) An APD cell corresponds to a lens in the lens array in one-to-one correspondence; and 5) Even if the lens does not correspond to the image sensor in one-to-one correspondence unlike the image sensor and the microlens array, improvement of the effective aperture ratio of the APD array can be anticipated owing to the light collection effect. However, the risk that a light ray is incident on the dead space of the APD array due to refraction remains. For leading light to the APD cell active region more certainly, it is desirable that the lens in the lens array corresponds to the APD cell in one-to-one correspondence.

In the present embodiment, it is not necessary to form an image on the active region by the lens, and consequently it is not necessary to collect light onto one point on the image sensor. Furthermore, if the lens is designed according to this feature, the lens face in the lens array is shrunk in size as the APD is shrunk in size. As the size is further shrunk, compatibility with a semiconductor process becomes better. As a result, it becomes possible to produce the APD array and the lens array and assemble in the same clean room.

Effectiveness of the lens array to the APD array and optimum conditions of the lens array will now be described using an optical simulation. Light ray tracking is used in the simulation.

(Construction of Simulation Model)

Figure 7:
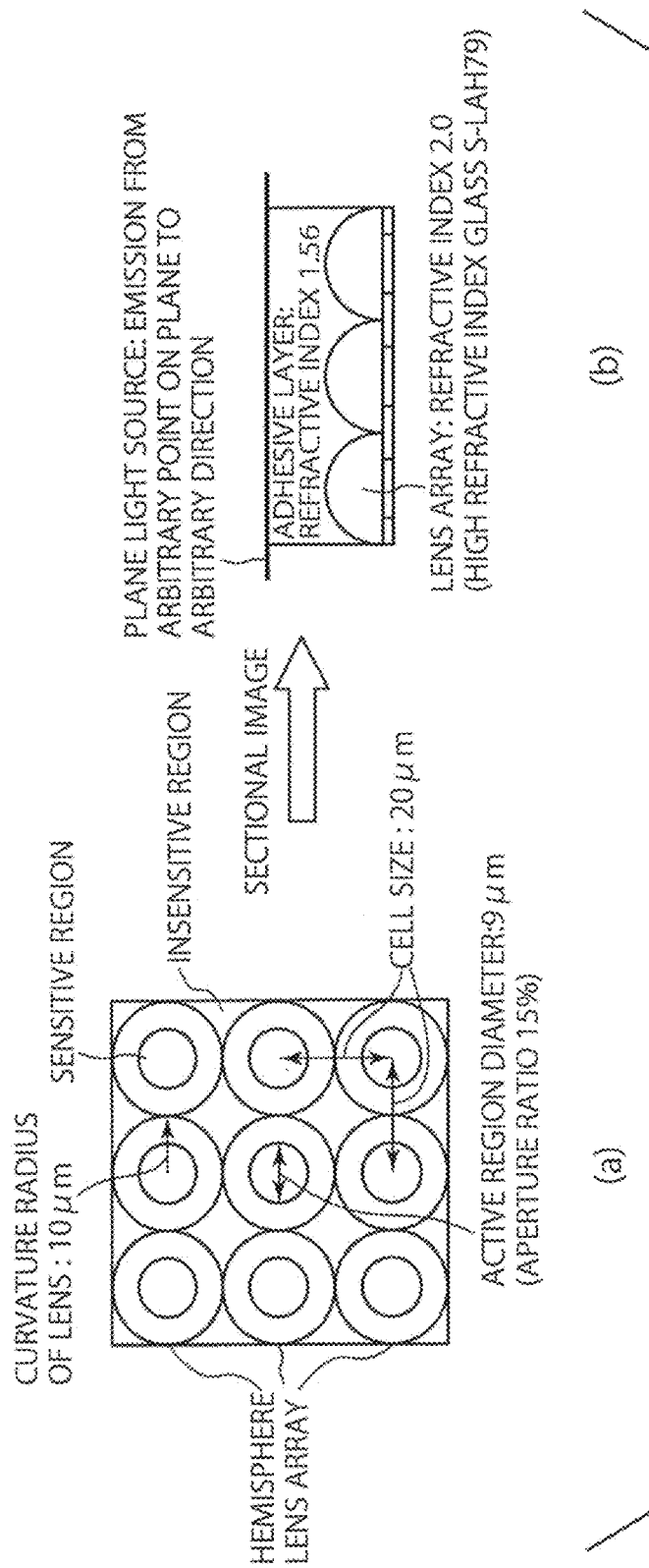
FIGS. 7(a) and 7(b) are diagrams for explaining a simulation model.

FIGS. 7(a) and 7(b) show an outline of a simulation model used in the present embodiment. In the simulation, a plane light source which radiates from an arbitrary point on a plane to an arbitrary solid angle within $2\pi$ is used. An APD array is installed right under (50 µm) the plane light source. The APD cell has a size of $20\times20$ µm$^2$, the active region (circular) has a radius of 4.5 µm, and the number of APD cells is $3\times3$. The aperture ratio of the APD cell in this case is 15%. A space between the APD array and the light source is filled with a material having a refractive index of 1.56 (an epoxy bonding agent is assumed). A lens is installed right above the APD cell in a form in contact with the APD cell, and the refractive index of the lens is changed as occasion demands. In the present embodiment, S-LAH 79 having a refractive index of 2.0 (see documents of Edmund Optics Inc.) is used and two values 1.5 and 1.6 are used as the refractive index of glass, in the simulation. Evaluation is conducted based on a difference in amount between light rays incident on the APD cell active region and light rays incident on outside of the active region. The evaluated region is a central region shown in FIGS. 8(a) and 8(b). The effective aperture ratio Ne is evaluated by using the following equation.

Ne=(an amount of light rays incident on the active region)/[(the amount of light rays incident on the active region)+(an amount of light rays incident on outside of the active region)/9]

By the way, it is assumed in the simulation that light rays are incident uniformly on the whole region on the APD array. Since the plane light source is used in the simulation in the present embodiment, this assumption is ensured.

Figure 8:
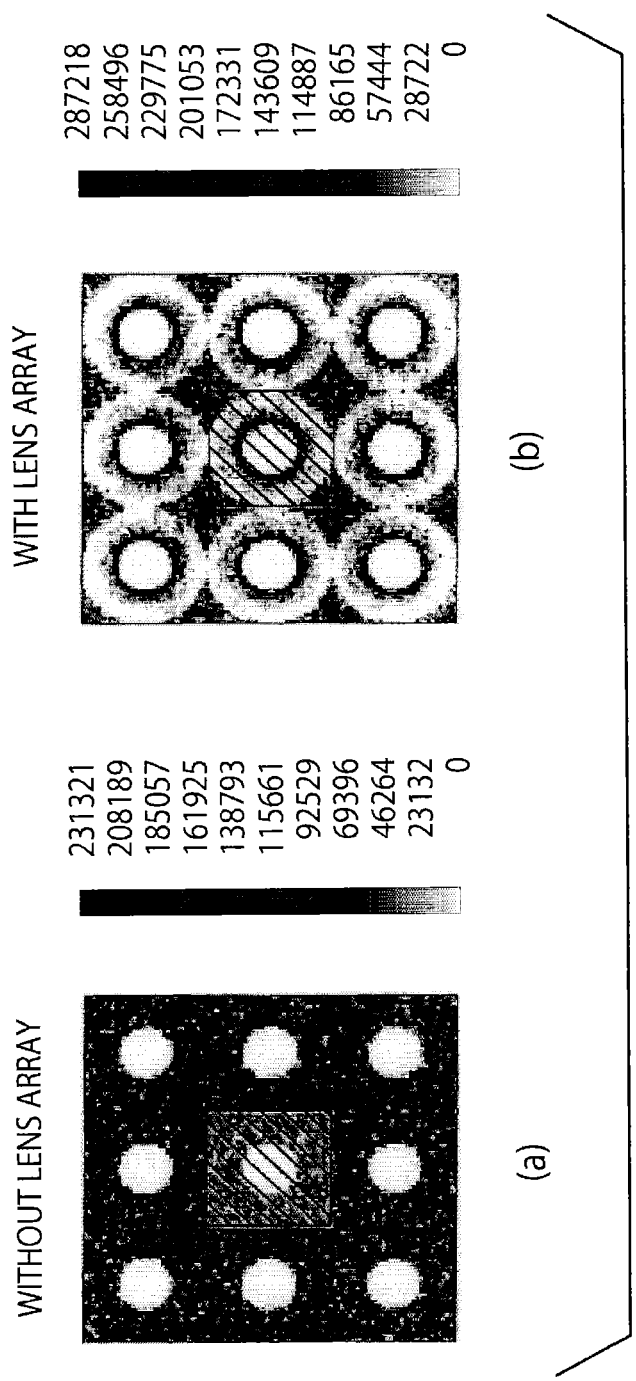
FIGS. 8(a) and 8(b) are diagrams for explaining effects of the first embodiment.

FIGS. 8(a) and 8(b) show results of a light ray tracking simulation in a case where a hemisphere lens having the APD cell size as its diameter is actually installed on the APD cell. FIG. 8(a) shows an image of the light ray tracking simulation result in a case where no lens array is provided, whereas FIG. 8(b) shows an image of the light ray tracking simulation result in a case where a lens array is provided. On the basis of this result, the effective aperture ratio is evaluated, and it is estimated to be 15.7% without a lens array and estimated to be 58.4% with a lens array. From this result, it is found that the ratio of arrival on the active region of the APD array cell becomes at least three times by providing the lens array. In other words, it is apparent that it is effective to install the lens array right above the APD cell as in the present embodiment.

(Optimum Lens Parameters)

Optimum lens parameters in a case where the APD cell is combined with a lens array which are found by the simulation will now be described.

a) Optimization by Simulation (Relation Between Lens Radius and Cell Size)

Figure 9:
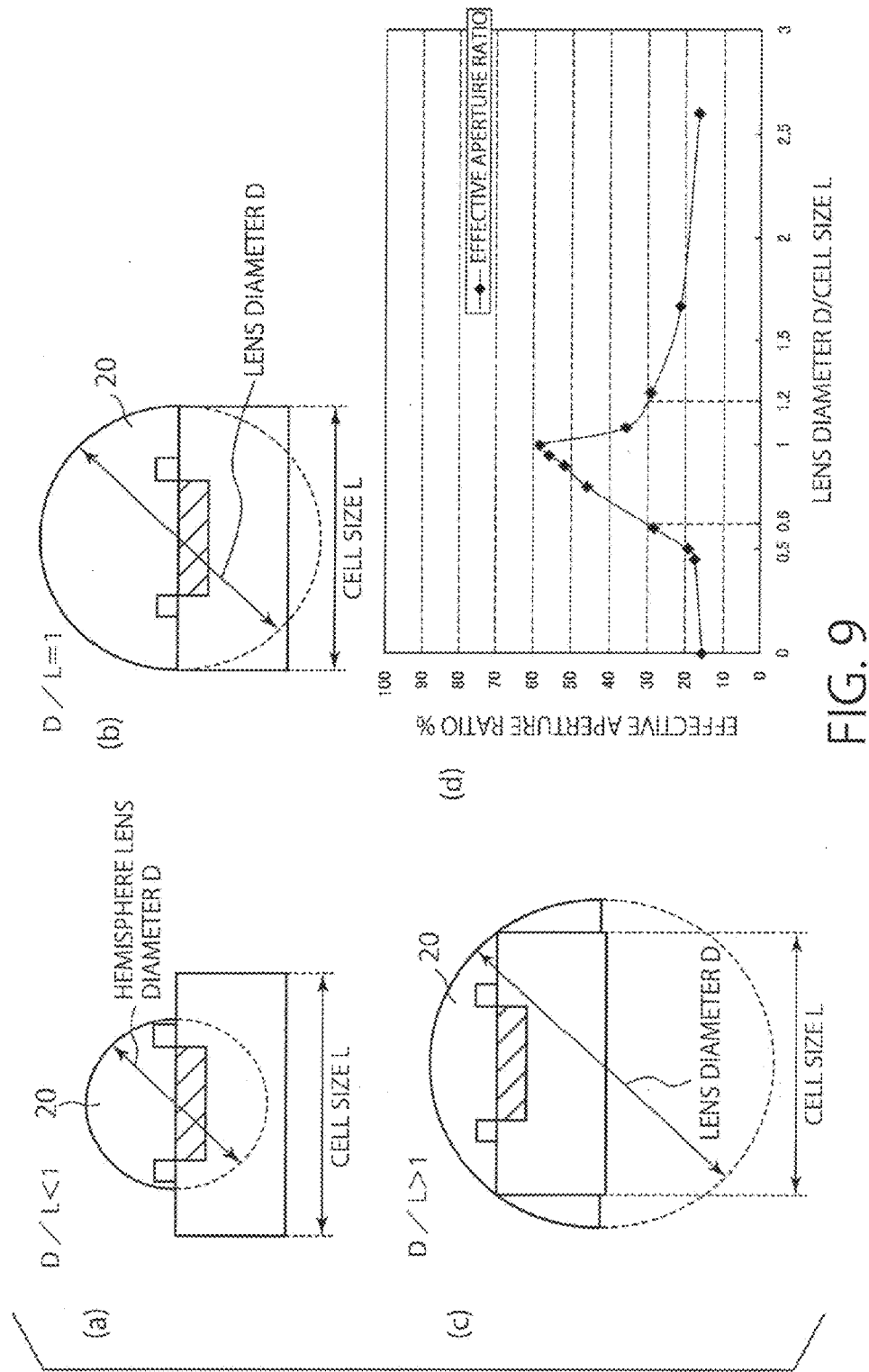
FIGS. 9(a) to 9(d) are diagrams for explaining relations between a lens diameter and a cell size.

As shown in FIGS. 9(a), 9(b), 9(c) and 9(d), the effective aperture ratio of the APD cell is evaluated by using a ratio D/L of a hemisphere lens diameter D to a cell size L. As for the APD cell, the conditions described with reference to FIGS. 7(a) and 7(b), i.e., the cell size of 20×20 μm² and the aperture ratio of 15% are used. FIGS. 9(a), 9(b) and 9(c) show sectional views of a cell in a case where the ratio D/L is less than 1.0, in a case where the ratio D/L is equal to 1.0, and in a case where the ratio D/L is greater than 1.0, respectively. FIG. 9(d) shows results of the simulation. As learned from FIG. 9(d), the effective aperture ratio becomes the highest when D/L=1, i.e., when the lens diameter is equal to the cell size. It is found by this simulation that the lens diameter which is the most effective for the APD array having the aperture ratio of 15% is equal to the cell size of the APD array. Furthermore, as learned from FIG. 9(d), the effective aperture ratio becomes at least 30% and it is desirable, if the ratio D/L is in the range of 0.6 to 1.2.

b) Optimization Based on Simulation (Relation Between Spherical Lens Height and Lens Curvature Radius)

Figure 10:
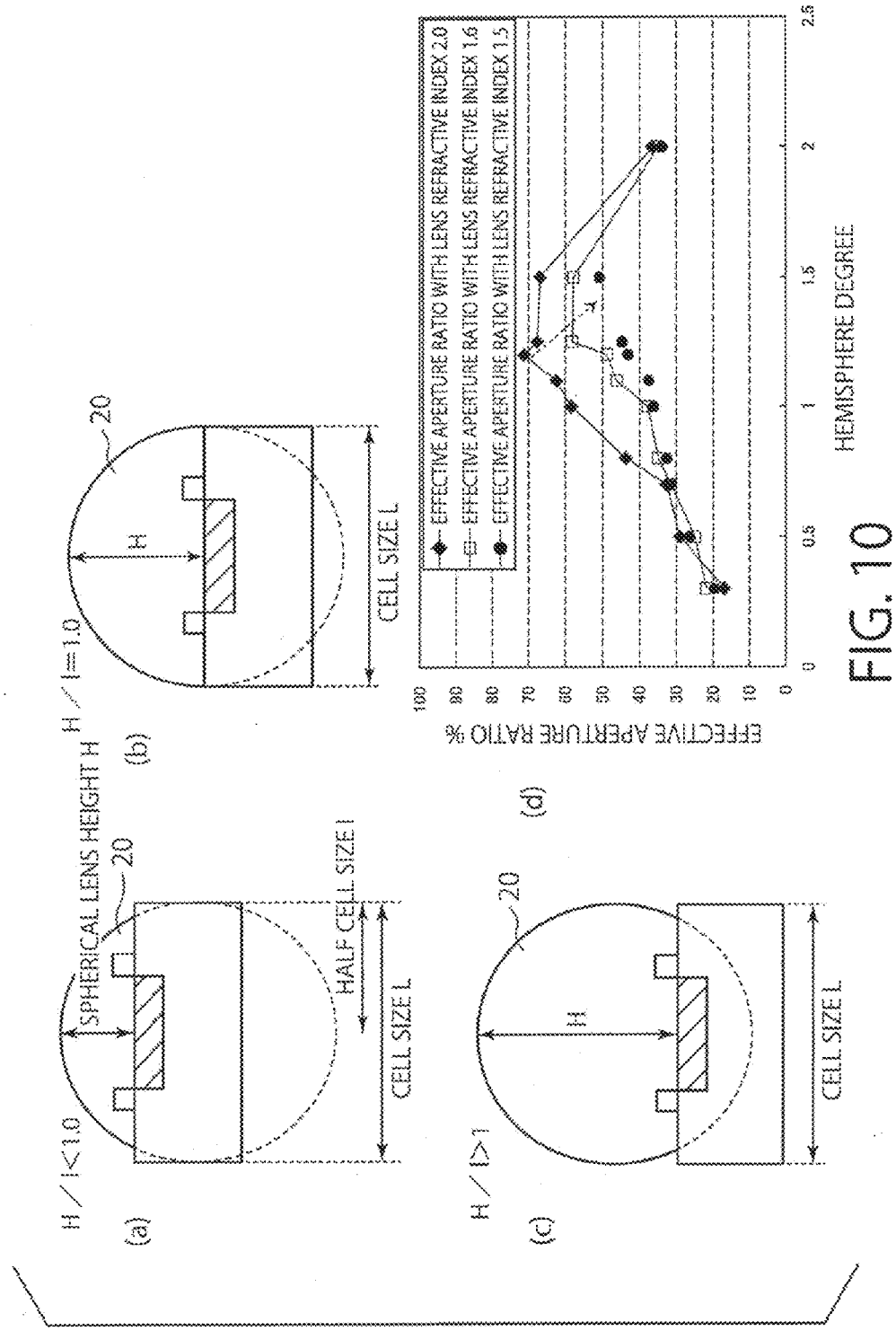
FIGS. 10(a) to 10(d) are diagrams for explaining relations between a lens height and a cell size.

As shown in FIGS. 10(a), 10(b), 10(c) and 10(d), the hemisphere degree of the lens is defined as H/l, where H is the height of the spherical lens located right above the APD array and l is the curvature radius of the lens. When H/l=1.0, the lens becomes a hemisphere. When H/l is greater than 1.0, the lens becomes close to a true sphere. FIGS. 10(a), 10(b), and 10(c) show sectional views of the cell in the case where a ratio H/l is less than 1.0, in a case where the ratio H/l is equal to 1.0, and in the case where the ratio H/l is greater than 1.0, respectively. FIG. 10(d) shows a result of relations between the hemisphere degree of the lens and the effective aperture ratio found by simulation with the refractive index chosen as a parameter. Since the effective aperture ratio has a peak with respect to the hemisphere degree as appreciated from FIG. 10(d), an optimum lens hemisphere degree exists. This evaluation is executed with respect to a lens having a lens refractive index of 2.0, a lens having a lens refractive index of 1.6, and a lens having a lens refractive index of 1.5. It is learned from the result that the optimum hemisphere degree differs every lens refractive index and the optimum hemisphere degree increases as the lens refractive index becomes lower. It is considered that this is caused because how incident light rays refract differs depending upon the difference in refractive index. Furthermore, as indicated by an arrow in FIG. 10(d), the peak shifts depending upon the refractive index of the lens.

c) Optimized APD Array and Lens Array

Figure 11:
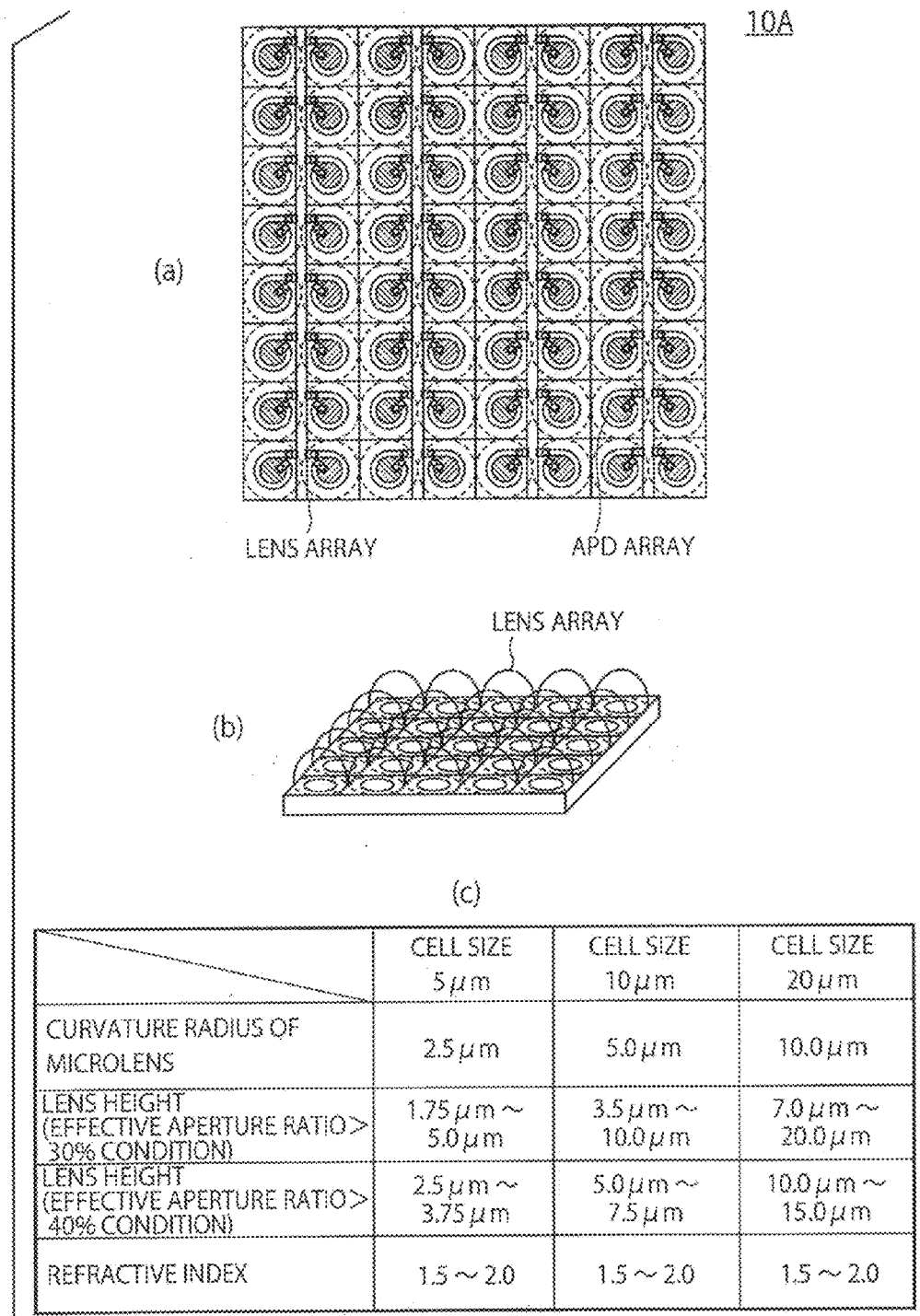
FIGS. 11(a), 11(b) and 11(c) are a plane view showing a case where lenses and cells are square-arranged, a perspective view, and a diagram showing optimum lens conditions.

FIGS. 11(a) and 11(b) show a first example of an optimum lens array structure introduced by the simulation. FIG. 11(a) shows a top view of the first example of the optimum lens array, and FIG. 11(b) shows its perspective view. The first example of the optimum lens array becomes a square arrangement. It should be noted that the structure of the square arrangement corresponds to the case where the optimization is executed for the APD cell having the aperture ratio which is as small as 15%. Examples of the optimum lens conditions are shown in FIG. 11(c). In the present embodiment, conditions in the case where a lens array is combined with an APD array which can be executed are shown.

If a condition that the effective aperture ratio Ne exceeds 30% is selected and the cell size is 5 μm, then the curvature radius of the lens array is estimated to be 2.5 μm and the lens height H is estimated to be in the range of 1.75 μm to 5.0 μm.

Under the condition that the effective aperture ratio Ne exceeds 40%, the lens height H is estimated to be in the range of 2.5 μm to 4.25 μm. In the case where the cell size is 10 μm or 15 μm as well, estimation is conducted in the same way.

From the foregoing description, the condition of the optimum lens is that the curvature radius of the lens is half of the cell size. Under the condition that the aperture ratio is greater than 30%, the hemisphere degree of the lens is in the range of 0.7 to 2.0. Furthermore, under the condition that the aperture ratio is greater than 40%, the hemisphere degree of the lens is in the range of 1.0 to 1.5.

Figure 12:
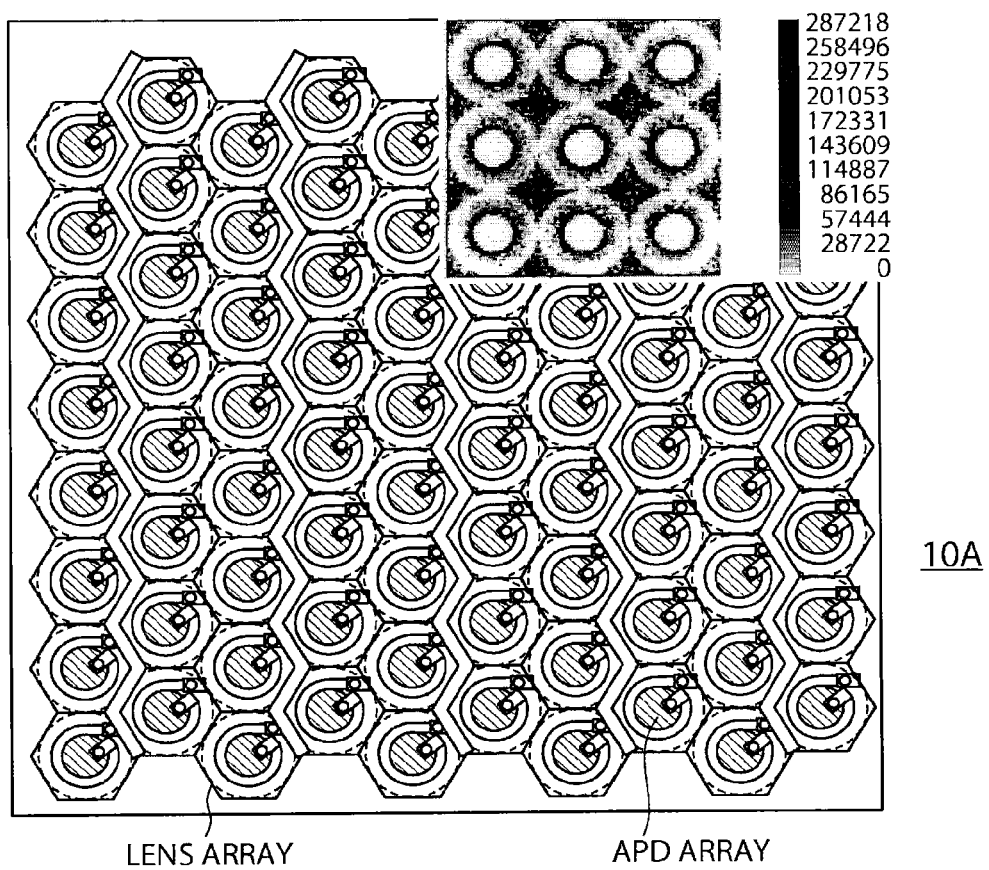
FIG. 12 is a plane view showing a case where lenses and cells are subject to hexagonal close-packed arrangement.

FIG. 12 shows a second example of an optimized combination of APD array and lens array. The second example is an arrangement in a case where a hexagonal close-packed structure is taken. If the APD cells are arranged in a square array as shown in a top right part of FIG. 12, then a dead space is caused between lenses because the lens is spherical. For utilizing light ray components incident on the dead space, the hexagonal close-packed structure as shown in FIG. 12 is desirable. Owing to the arrangement of the hexagonal close-packed structure, it becomes possible to make the dead space between lenses small and light rays can be utilized more effectively.

(Manufacturing Method of Lens Array)

Figure 13:
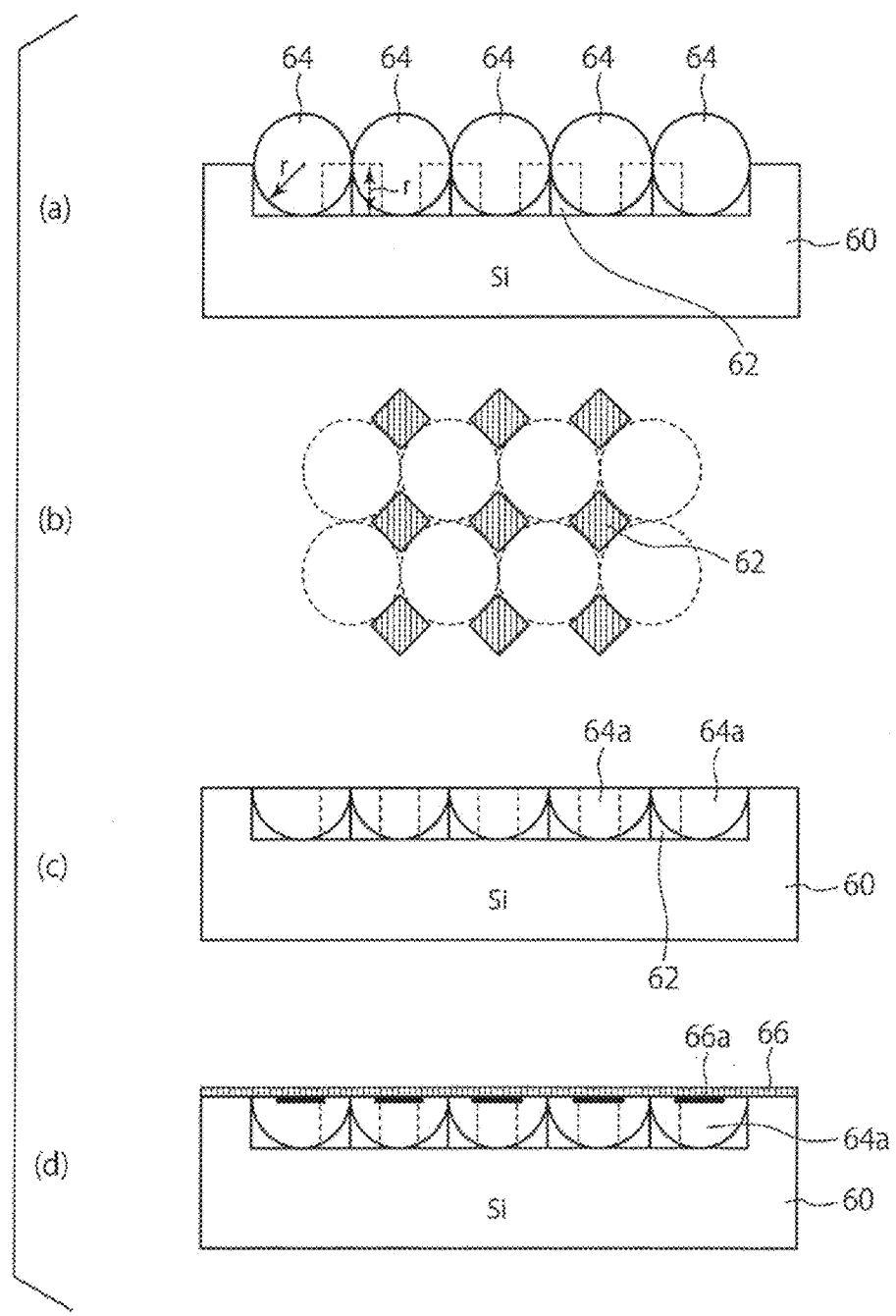
FIGS. 13(a) to 13(d) are diagrams for explaining a manufacturing method of a lens array.

The manufacturing method of the lens array will now be described with reference to FIGS. 13(a) to 13(d). As shown in FIG. 13(a), a groove etched to have a desired depth as the lens height is formed on a Si wafer 60, and silica beads 64 are lined up in a self-aligned manner in the groove. If the silica beads are disposed in the groove with the hexagonal close-packed structure, it is not necessary to provide struts in the groove. If the silica beads are disposed in the square arrangement, however, struts 62 become necessary as shown in FIGS. 13(a) and 13(b). In this case, it is desirable that the struts 62 are square pillars.

In this way, the silica beads 64 are lined up in the groove of the Si wafer 60. Then, the silica beads 64 are etched by utilizing a selection ratio of Si to the silica beads. Subsequently, planarization is conducted (FIG. 13(c)).

Then, a light sensing element array 66 with active regions 66a formed thereon is mounted. When conducting the mounting, marking for making a position deviation small is utilized suitably.

According to the first embodiment, it is possible to count visible light without omission and it is possible to obtain a radiation detection apparatus capable of increasing the detection efficiency of fluorescent light emitted from a fluorescent material, as described heretofore.

Second Embodiment

A radiation detection apparatus according to a second embodiment will now be described. In the radiation detection apparatus according to the second embodiment, the scintillator light taken-out efficiency is improved by disposing a projection structure in the taken-out part. When taking out light generated in the scintillator, the taken-out efficiency depends upon mismatching between a refractive index of a junction part filled between the scintillator and the sensor and a refractive index of the scintillator. Since this is determined at the time when selecting materials, it is necessary to study a structure which makes it possible to use a large solid angle to take out light.

As a result of eager studies, therefore, the present inventors have hit upon an idea that it becomes possible to make a solid angle which can be used to take out light largely by using a pyramidal projection structure in the scintillator light taken-out part. And the present inventors have confirmed validity of this idea by conducting simulation. This idea and its optimum structure will now be described in the second embodiment.

Figure 14:
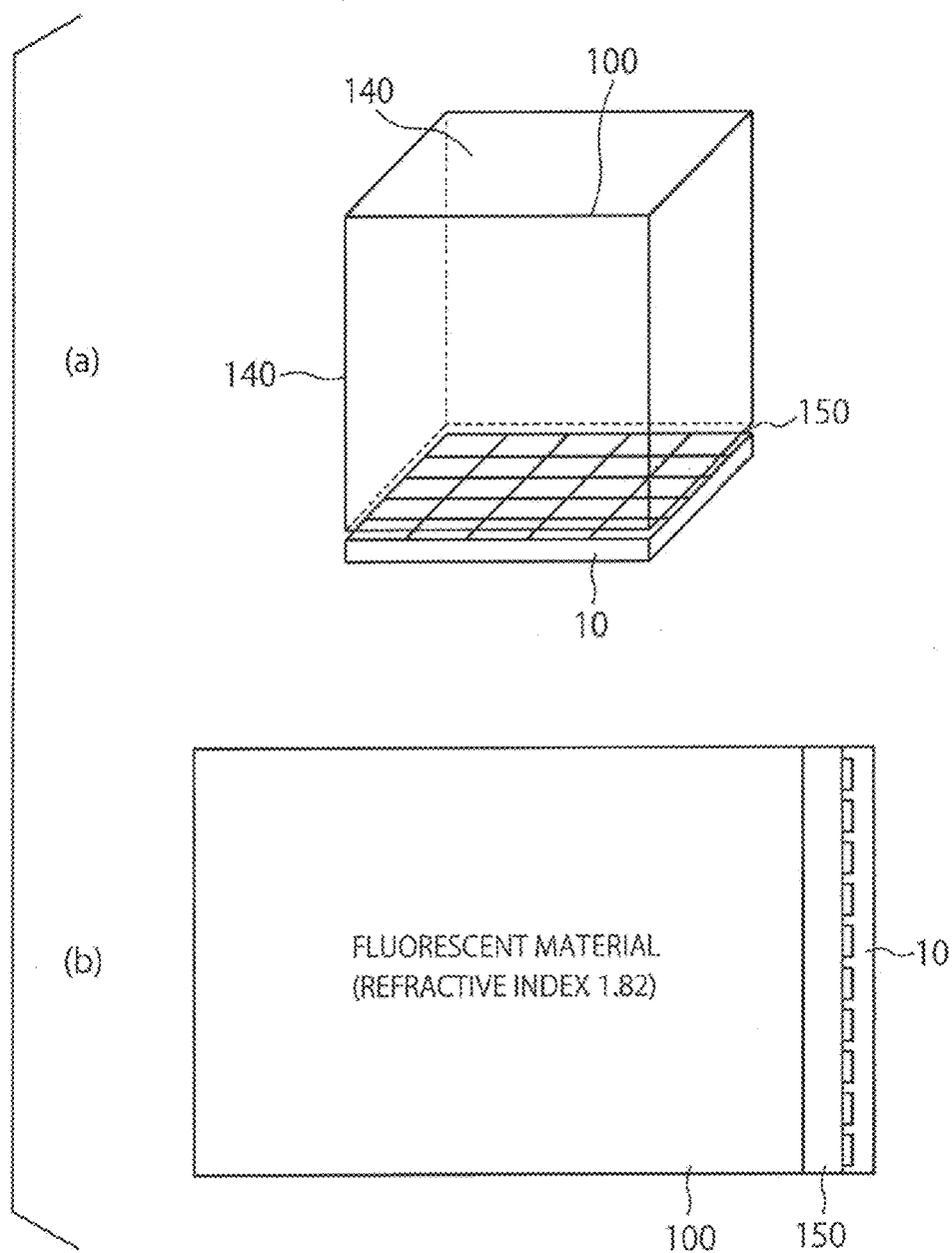
FIGS. 14(a) and 14(b) are diagrams for explaining a problem of a light taken-out efficiency of a scintillator.

FIGS. 14(a) and 14(b) show a perspective view and a sectional view of a basic scintillator 100—an adhesive layer 150—an APD array 10, respectively. A high reflectance material 140 is painted on side faces and a radiation incidence part of the scintillator 100. In the simulation, therefore, coating of a reflectance of 98% is defined. Furthermore, as for the adhesive layer 150, epoxy (refractive index 1.56) which is a typical bonding agent is used, and its thickness is set equal to 50 µm. As for the size of the scintillator 100, 0.5×0.5×2 mm$^2$, use of which in the CT/PET is being studied, is used. If nothing is executed on the scintillator, the light taken-out efficiency is approximately 45%.

(Light Taken-Out Structure Using Scintillator Structure and Pyramidal Structure and Optimization Using Simulation)

Figure 15:
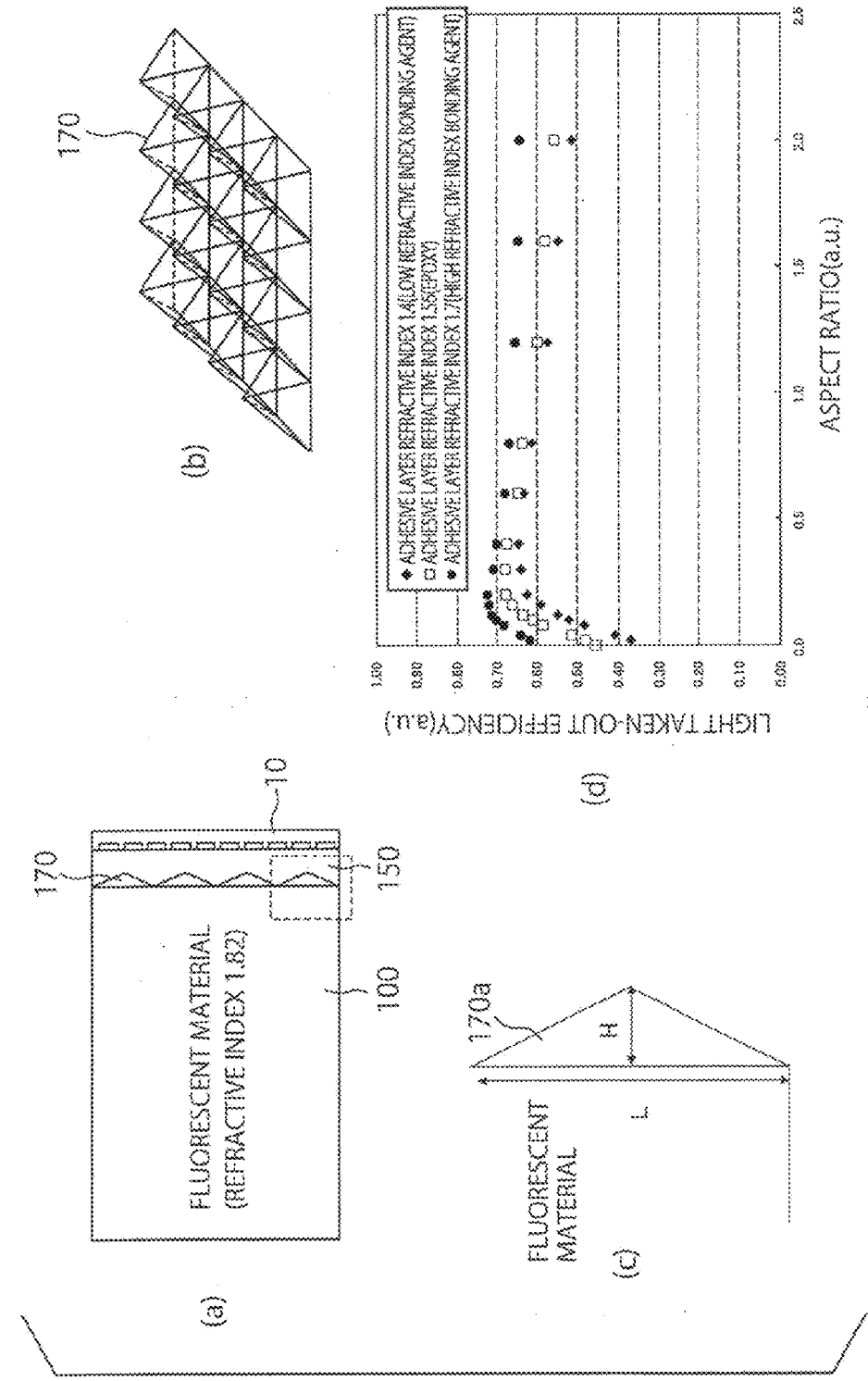
FIGS. 15(a) to 15(d) are diagrams for explaining a radiation detection apparatus according to a second embodiment.

As shown in FIG. 15(a), a pyramidal projection structure 170 is disposed on a face of the scintillator 100 opposed to the APD array 10. In the present embodiment, the projection structure 170 is a quadrangular pyramid structure as shown in FIG. 15(b). The projection structure 170 has a refractive index which is equal to that of the scintillator 100. Since LYSO is used as the scintillator in the simulation, the refractive index is 1.82. It is supposed in this structure that a bottom face of each component 170a in the projection structure 170 is a square which is L in one side length and the quadrangular pyramid has a height of H as shown in FIG. 15(c). The light taken-out efficiency is evaluated as a function of an aspect ratio H/L by simulation. A result of this evaluation is shown in FIG. 15(d). Black rhombuses represent results in a case where a bonding agent having a low refractive index 1.4 is used. White squares represent results in a case where epoxy resin having a refractive index 1.56 is used. Black circles represent results in a case where a bonding agent having a high refractive index 1.7 is used. When the aspect ratio is in the range of 0.1 to 0.5, the light taken-out efficiency exceeds 60% regardless of the refractive index of the material used in the adhesive layer 150, as shown in FIG. 15(d).

(Scintillator and Pyramid Structure)

Figure 16:
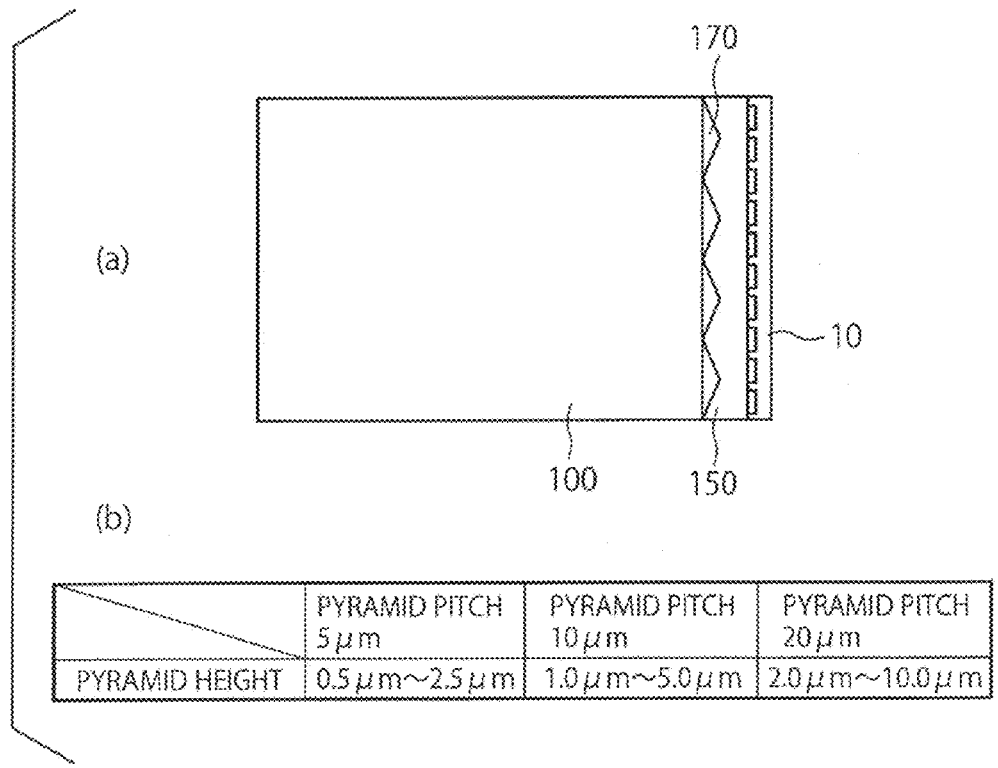
FIGS. 16(a) and 16(b) are diagrams showing an example of a radiation detection apparatus according to the second embodiment.

FIG. 16(a) shows a sectional view of the radiation detection apparatus according to the second embodiment. The radiation detection apparatus according to the second embodiment includes the scintillator 100, the projection structure 170 provided on a light taken-out side of the scintillator 100, and the APD array 10. The APD array 10 and the projection structure 170 are bonded together by the adhesive layer 150.

In the second embodiment, the light taken-out efficiency depends upon the aspect ratio H/L regardless of the number of pyramid arrays in the projection structure 170. The projection structure 170 is, for example, a quadrangular pyramid, and the aspect ratio H/L defined by one side L of the bottom face of the quadrangular pyramid and the height H is desired to be in the range of 0.1 to 0.5. A desirable aspect ratio depends upon the refractive index of the adhesive layer 150 provided between the scintillator 100 and the APD array 10. The range of 0.1 to 0.5 of the desirable aspect ratio is a range which yields the light taken-out efficiency of 60% in a case where the adhesive layer 150 in the range of the low refractive index (at least 1.4 and less than 1.55) to the high refractive index (at least 1.55 and at most 1.7) is used.

The light taken-out efficiency depends upon the aspect ratio H/L in this way. In a case where the projection structure 170 is combined with the APD array 10, an optimized structure can be taken independently. As a suitable range of the projection structure 170, a range of the pyramid height H is shown in FIG. 16(b) with respect to each of values 5 µm, 10 µm and 20 µm of a pitch (length of one side of the bottom face) L of the quadrangular pyramid (also referred to as pyramid).

As the size of the projection structure 170 shrinks, compatibility with the semiconductor process is improved. However, it is desirable that the projection structure 170 is a structure which is greater than the wavelength of light. Furthermore, as the projection structure 170, for example, a cone structure or a polygonal pyramid structure can be used. In a case of the cone structure, a flat plane appears at the time of spatial filling and consequently the surface of the scintillator cannot be buried with projection structures leaving no space. In a case of the polygonal pyramid structure, it is possible to bury the surface of the scintillator leaving no space. For example, a hexagonal pyramid or the like may be used. In this case as well, dead spaces of pyramid structures occur on the plane of the scintillator side in the same way as the case of the cone structure. This can be solved by, for example, using a scintillator of hexagonal pillar type.

According to the second embodiment, it is possible to improve the scintillator light taken-out efficiency and it is possible to obtain a radiation detection apparatus capable of increasing the detection efficiency of fluorescent light emitted from the fluorescent material, as described heretofore.

Third Embodiment

Figure 17:
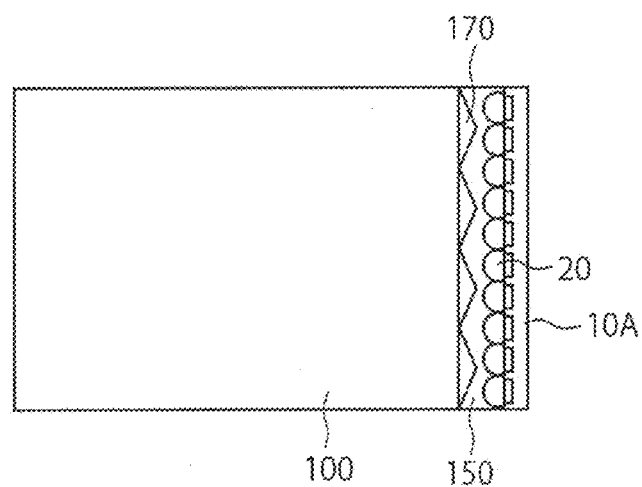
FIG. 17 is a sectional view showing a radiation detection apparatus according to a third embodiment.

A radiation detection apparatus according to a third embodiment is shown in FIG. 17. The radiation detection apparatus according to the third embodiment has a configuration obtained by combining the radiation detection apparatus according to the first embodiment with the radiation detection apparatus according to the second embodiment. In other words, the radiation detection apparatus according to the third embodiment includes the scintillator 100, the APD array 10A described in the first embodiment, and the projection structure 170 provided on a face of the scintillator opposed to the APD array 10A. By the way, the projection structure 170 and the APD array 10A are glued together by the adhesive layer 150.

The light taken-out efficiency of the whole system which is less than 10% before combination becomes at least 40% by adopting such a configuration.

A lens diameter D of a lens 20 provided in the APD array 10A depends upon the size L of the APD cell in the APD array, and it is desirable that D=L. Furthermore, it is desirable that the height of the lens 20 is in the range of 0.7 to 2.0 times the lens radius. If conditions are set to make the effective aperture ratio at least 40%, it is desirable that the height H of the lens 20 is in the range of 1.0 to 1.5 times the lens radius R.

According to the third embodiment, it is possible to count visible light without omission and improve the scintillator light taken-out efficiency, and it is possible to obtain a radiation detection apparatus capable of increasing the detection efficiency of fluorescent light emitted from the fluorescent material, as described heretofore.

Fourth Embodiment

Figure 18:
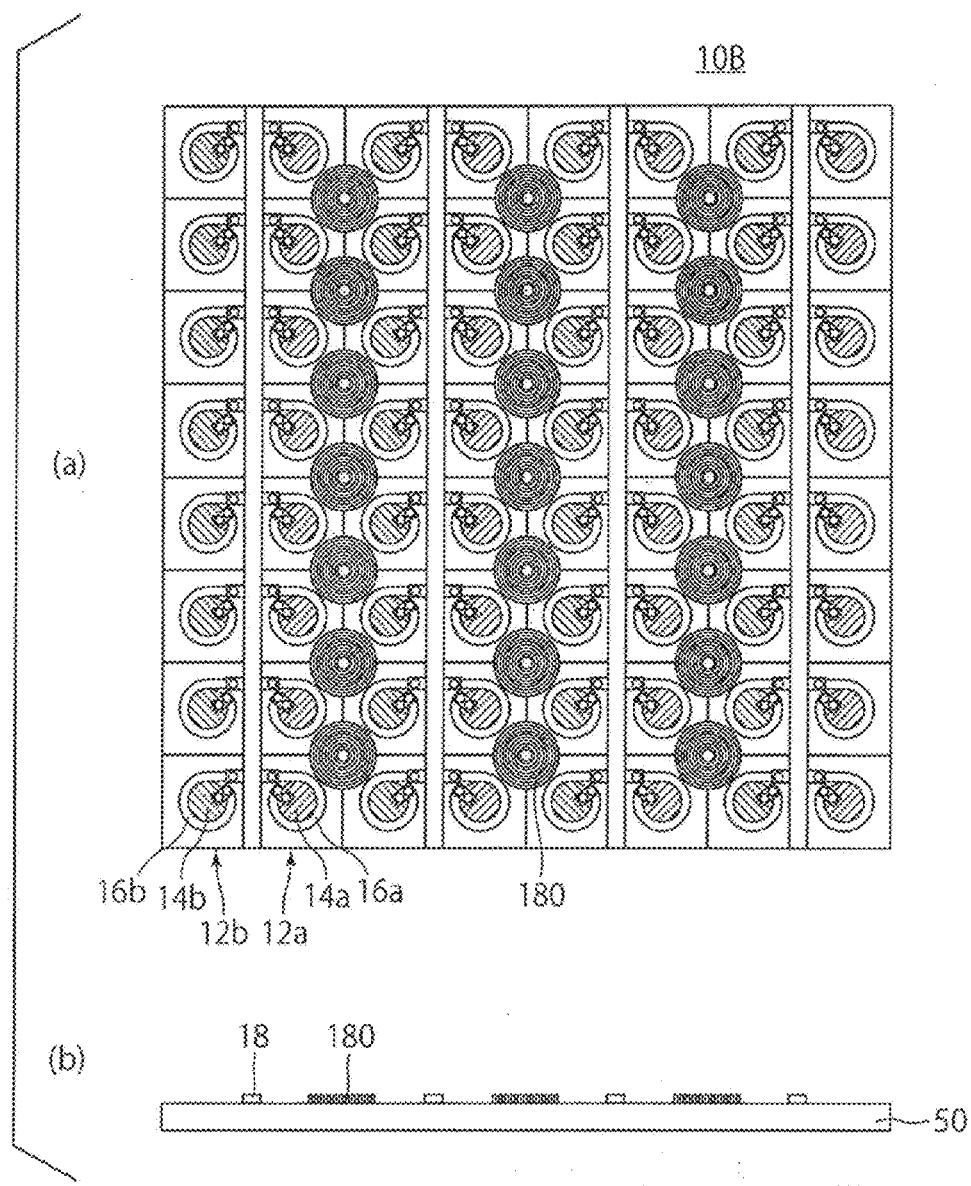
FIGS. 18(a) and 18(b) are a plane view and a sectional view showing an APD array in a radiation detection apparatus according to a fourth embodiment.

A radiation detection apparatus according to a fourth embodiment will now be described with reference to FIGS. 18(a) and 18(b). The radiation detection apparatus according to the fourth embodiment has a configuration obtained from that of the radiation detection apparatus according to the first embodiment by replacing the APD array 10A with an APD array 10B shown in FIG. 18(a). This APD array 10B has a configuration obtained by removing the lenses from the APD array 10A and providing a reflective grating (diffraction grating) 180 in the dead space of the APD cell. As shown in FIG. 18(b), this grating 180 is provided on a semiconductor substrate 50 having the active regions 14a and 14b and the resistors 16a and 16b formed thereon.

In the fourth embodiment, the reflective grating 180 is provided in the dead space which becomes large as the size of the cell shrinks, as shown in FIG. 18(b). If light incident on the dead space is subject to regular reflection, improvement of the utilization efficiency of light is slight. By using light scattering caused by the grating 180, however, it becomes possible to cause reflected light to be incident on the APD active regions 14a and 14b again (see FIG. 19).

Although there are regular reflection components in the grating 180, it has first order to nth order diffracted light. As a result, it becomes possible to improve the incidence probability of photons by scattering. If a scintillator which emits blue light, such as LYSO, is used, it is desirable to set the grating constant in the range of 600 nm to 1,000 nm. Owing to this structure, it is possible to place approximately 20 gratings in a dead space region of 10×10 µm$^2$. As a result, it becomes possible to improve the light taken-out efficiency by utilizing the diffraction phenomenon.

By the way, the grating 180 is formed by, for example, etching a metal film and thereby forming unevenness having a depth of approximately 1 µm.

Figure 19:
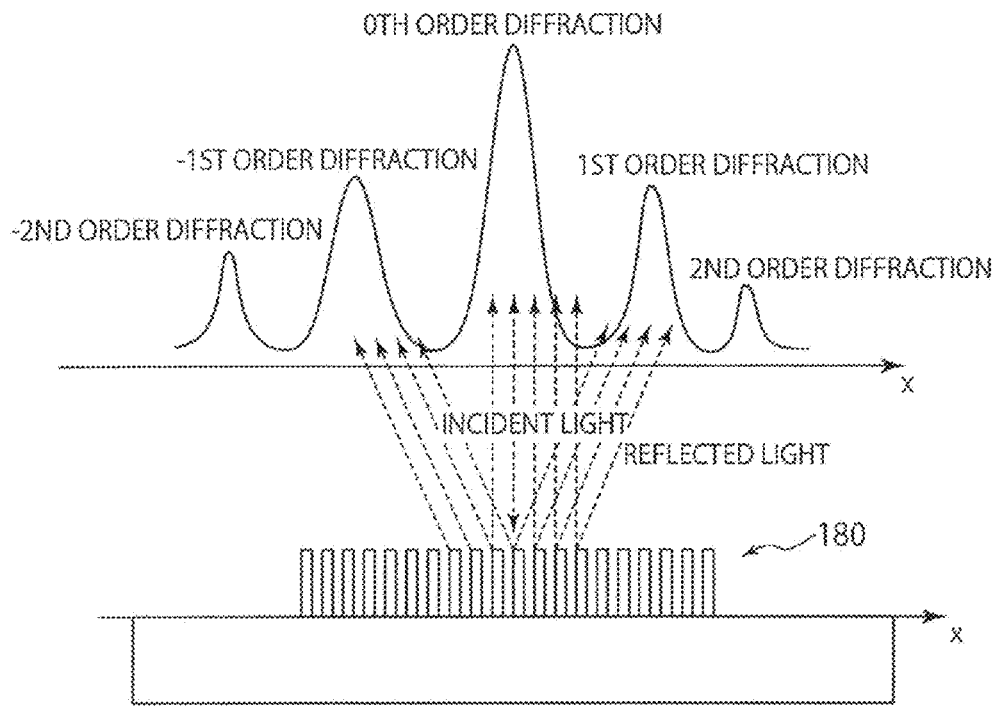
FIG. 19 is a diagram for explaining distribution of reflected light caused by a diffraction effect of a grating.

As shown in FIG. 19, it is possible to reflect incident light to a certain angle direction efficiently and lead light rays to the light sensing element by using a grating constant in the range of approximately 600 nm to 1,000 nm. It is desirable that the grating 180 has a height in the range of 1 µm to 2 µm. If the aperture ratio is approximately 15%, a dead space of approximately 10×10 µm$^2$ exists in the cell area. Approximately 10 to 20 gratings can be placed in the dead space.

According to the fourth embodiment, it is possible to utilize light incident on the dead space and it is possible to obtain a radiation detection apparatus capable of increasing the detection efficiency of fluorescent light emitted from a fluorescent material.

Furthermore, the grating 180 described in the fourth embodiment can be used in the radiation detection apparatuses according to the first to third embodiments.

Fifth Embodiment

Figure 20:
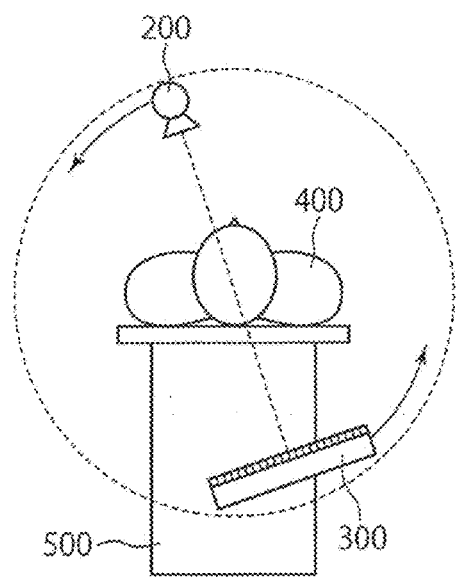
FIG. 20 is a schematic diagram for explaining a CT according to a fifth embodiment.
Figure 21:
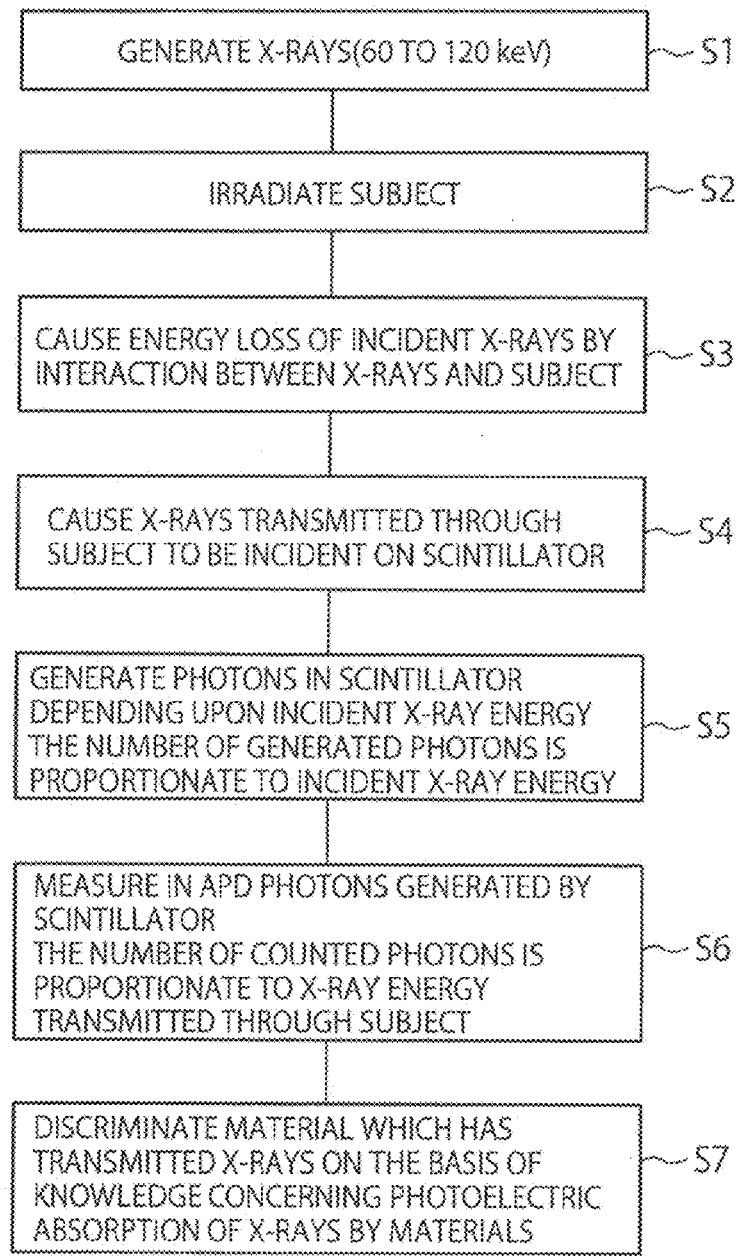
FIG. 21 is a flow chart for explaining an operation procedure of a CT according to the fifth embodiment.

A computer tomography (CT) system according to a fifth embodiment is shown in FIG. 20. The CT system includes an X-ray generation apparatus 200 and a radiation detection apparatus 300. The radiation detection apparatus 300 is a radiation detection apparatus according to any of the first to fourth embodiments. X-rays are emitted from the X-ray generation apparatus 200 to a subject 400 lying on a table 500. X-rays transmitted through the subject 400 and attenuated are detected by the radiation detection apparatus 300, and X-ray imaging is obtained. Its procedure is shown in FIG. 21. First, X-rays in the range of 60 keV to 120 keV are generated by the X-ray generation apparatus 200, and the subject 400 is irradiated with the X-rays (steps S1 and S2). While the X-rays are transmitted by the subject 400, the X-ray energy is attenuated by interaction between the X-rays and the subject (step S3). The X-rays transmitted by the subject 400 and attenuated are incident the scintillator in the radiation detection apparatus 300 (step S4). Photons are generated in the scintillator according to the energy of the incident X-ray photons (step S5). The generated photons are measured by the APDs (step S6). A material which has transmitted the X-ray photons is discriminated on the basis of knowledge concerning photoelectric absorption of X-ray photons by materials (step S7).

The CT system according to the fifth embodiment uses a radiation detection apparatus according to any of the first to fourth embodiments having a high fluorescent light detection efficiency as the radiation detection apparatus. As a result, the amount of X-rays generated by the X-ray generation apparatus can be reduced.

While certain embodiments have been described, these embodiments have been presented by way of example only, and are not intended to limit the scope of the inventions. Indeed, the novel methods and systems described herein can be embodied in a variety of other forms; furthermore, various omissions, substitutions and changes in the form of the methods and systems described herein can be made without departing from the spirit of the inventions. The accompanying claims and their equivalents are intended to cover such forms or modifications as would fall within the scope and spirit of the inventions.

What is claimed is:

1. A radiation detection apparatus, comprising:
   a scintillator including a fluorescent material to convert radiation to visible radiation photons;
   a photon detection device array having a plurality of cells each of which includes a photon detection device to detect visible radiation photons emitted from the fluorescent material in the scintillator and convert the visible radiation photons to an electric signal, the photon detection device being an avalanche photodiode of pn-junction type, each of the plurality of cells further comprising resistors provided to surround active regions of the avalanche photodiode; and
   a plurality of lenses provided on cells respectively in association with the cells to cause the visible radiation photons to be incident on the photon detection device in an associated cell.

2. The apparatus according to claim 1, wherein each of the plurality of lenses is a lens which is convex on an incidence side of the visible radiation photons.

3. The apparatus according to claim 2, wherein a ratio 2r/l is in a range of 0.6 to 1.2, where r is a curvature radius of each of the plurality of lenses and l is a size of each of the plurality of cells.

4. The apparatus according to claim 2, wherein a ratio of a height of each of the plurality of lenses to a curvature radius of each of the plurality of lenses is in a range of 1.0 to 1.5.

5. The apparatus according to claim 1, comprising a projection structure provided on a visible radiation photon emitting face of the scintillator.

6. The apparatus according to claim 5, wherein
the projection structure has a plurality of polygonal pyramid projection parts,
the projection parts are arranged on a face of emission of the visible radiation photons of the scintillator, and
a ratio of a height of each of the projection parts to a length of one side of a bottom face of each of the projection parts is in a range of 0.1 to 0.5.

7. The apparatus according to claim 1, wherein reflective members are provided in regions of the plurality of cells except the active regions and the resistors to reflect visible light.

8. The apparatus according to claim 7, wherein each of the reflective members is a grating.

9. A radiation detection apparatus comprising:
a scintillator having a fluorescent material to convert radiation to visible radiation photons;
a projection structure provided on a visible radiation photon emitting face of the scintillator;
a photon detection device array having a plurality of cells each of which includes a photon detection device to detect visible radiation photons emitted from a fluorescent material in the scintillator and convert the visible radiation photons to an electric signal; and
a plurality of lenses provided on cells respectively in association with the cells to cause the visible radiation photons to be incident on the photon detection device in an associated cell, wherein
the projection structure has a plurality of polygonal pyramid projection parts,
the projection parts are arranged on a face of emission of the visible radiation photons of the scintillator, and
a ratio of a height of each of the projection parts to a length of one side of a bottom face of each of the projection parts is in a range of 0.1 to 0.5.

10. A radiation detection apparatus comprising:
a scintillator having a fluorescent material to convert radiation to visible radiation photons;
a projection structure provided on a visible radiation photon emitting face of the scintillator;
a photon detection device array having a plurality of cells each of which includes a photon detection device to detect visible radiation photons emitted from a fluorescent material in the scintillator and convert the visible radiation photons to an electric signal; and
a plurality of lenses provided on cells respectively in association with the cells to cause the visible radiation photons to be incident on the photon detection device in an associated cell,
wherein the photon detection device is an avalanche photodiode of pn-junction type, and each of the plurality of cells further comprises resistors provided to surround active regions of the avalanche photodiode.

11. The apparatus according to claim 10, wherein reflective members are provided in regions of the plurality of cells except the active regions and the resistors to reflect visible light.

12. The apparatus according to claim 11, wherein each of the reflective members is a grating.

* * * * *